United States Patent [19]
Niimura et al.

[11] Patent Number: 5,547,973
[45] Date of Patent: Aug. 20, 1996

[54] METHOD OF INHIBITING AROMATASE

[75] Inventors: Koichi Niimura, Saitama; Takao Ando, Yamanashi; Toyohiko Nitta, Ibaraki; Yuko Ikeda, Chiba, all of Japan

[73] Assignee: Kureha Chemical Industry Co., Ltd., Tokyo, Japan

[21] Appl. No.: 486,142

[22] Filed: Jun. 7, 1995

Related U.S. Application Data

[63] Continuation-in-part of Ser. No. 137,045, Oct. 14, 1993, Pat. No. 5,489,597.

[30] Foreign Application Priority Data

Feb. 15, 1992 [JP] Japan .................................. 4-61441
Feb. 12, 1993 [WO] WIPO .................... PCT/JP93/00181

[51] Int. Cl.⁶ .................. A61K 31/415; C07D 233/60
[52] U.S. Cl. ........................... 514/399; 548/341.1
[58] Field of Search ................... 514/399; 548/341.1

[56] References Cited

FOREIGN PATENT DOCUMENTS

| | | |
|---|---|---|
| 0324646 | 7/1989 | European Pat. Off. . |
| 0413448 | 2/1991 | European Pat. Off. . |
| 3197464 | 8/1991 | Japan . |

*Primary Examiner*—Patricia L. Morris
*Attorney, Agent, or Firm*—Sughrue, Mion, Zinn, Macpeak & Seas

[57] ABSTRACT

A method of inhibiting aromatase, comprising administering to a mammal in need thereof a pharmaceutical composition comprising an effective aromatase inhibiting amount of a compound of the formula (I):

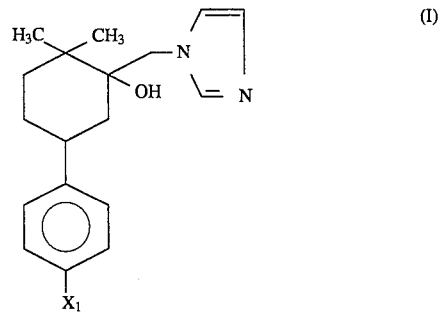

wherein $X_1$ is a chlorine or fluorine atom, or a hydroxy group, or a pharmaceutically acceptable salt thereof, and a pharmaceutically acceptable carrier.

14 Claims, No Drawings

METHOD OF INHIBITING AROMATASE

CROSS REFERENCE TO RELATED APPLICATION

This is a continuation-in-part application of patent application Ser. No. 08/137,045 filed on Oct. 4, 1993, now U.S. Pat. No. 5,489,597, which was derived from International Patent Application No. PCT/JP93/00181 filed on Feb. 12, 1993.

BACKGROUND OF THE INVENTION

1. Field of the Invention

The present invention relates to a method of inhibiting aromatase by administering a novel imidazole derivative as an active ingredient.

2. Description of the Related Art

The recent development of pharmaceuticals and the advancement of medical techniques conquered many diseases. On the other hand, such treatment caused the depression in the immune systems. The depression became a major cause of the increase in patients susceptible to infection. These patients suffered at a high rate from deep-seated fungal diseases of opportunistic infections such as candidiasis, aspergillosis, and cryptococcosis. The measure to solve the problem became serious. Therefore, active research has been under way to develop drugs more superior than the conventional antifungal agents. For example, Japanese Unexamined Patent Publication (Kokai) No. 3-187464 discloses an azole derivative having a cyclohexanol ring and azole ring as basic structures. Such antifungal agents exhibit an antifungal activity by functioning on the cytochrome p450 in the fungus and inhibiting the production of ergosterol which is a constituent element of cell walls. Further, it is known that because the above antifungal agents function on the cytochrome p450, some of them exhibit an activity to inhibit aromatase [*J. Med. Chem.*, 33 (11), 2933–2942 (1990)].

From the results of the research on azole derivatives having applicability to broader fields and exhibiting a more superior antimicrobial activity, the inventors of the present invention found a novel imidazole derivative which has a low toxicity, and which exhibits activity against many fungi, and activity to inhibit an aromatase. The present invention is based on the above findings.

SUMMARY OF THE INVENTION

Therefore, the present invention relates to a method of inhibiting aromatase, comprising administering to a mammal in need thereof a pharmaceutical composition comprising an effective aromatase inhibiting amount of a compound of the formula (I):

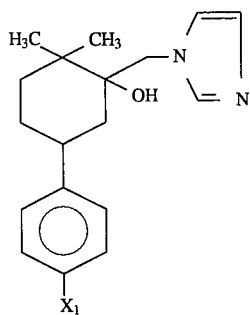

wherein $X_1$ is a chlorine or fluorine atom, or a hydroxy group, or a pharmaceutically acceptable salt thereof, and a pharmaceutically acceptable carrier.

DETAILED DESCRIPTION OF THE PREFERRED EMBODIMENTS

The imidazole derivative of the formula (I) [hereinafter sometimes referred to as the present compound (I) or the present imidazole compound (I)] may be prepared, for example, from a compound of the formula (V):

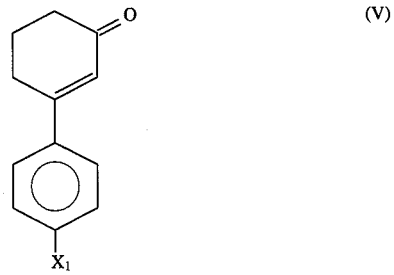

wherein $X_1$ has the same meaning as above, by a process comprising the following steps (a), (b), and (c).

(a) The compound of the formula (V) is reduced to obtain the compound of the formula (IV) [hereinafter sometimes referred to as the cyclohexanone compound (IV)]:

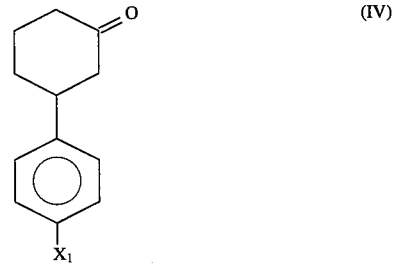

wherein $X_1$ has the same meaning as above.

(b) The resulting cyclohexanone compound (IV) is reacted with an S-ylide compound to obtain the compound of the formula (III) [hereinafter sometimes referred to as the oxolane compound (III)]:

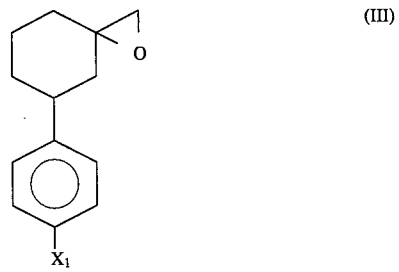

wherein $X_1$ has the same meaning as above.

(c) The oxolane compound (III) is reacted with the imidazole of the formula (II):

wherein M is a metal ion, for example, an alkali metal ion, such as sodium or potassium ion, thereby obtaining the present imidazole compound (I).

As the diluents which may be used in the series of reactions in the steps (a), (b), and (c), there may be mentioned hydrocarbons, such as benzene, toluene, xylene or hexane; halogenated hydrocarbons, such as methylene chloride, chloroform or carbon tetrachloride; alcohols, such as methanol, ethanol or isopropyl alcohol; ethers, such as diethyl ether, diisopropyl ether, tetrahydrofuran or dioxane; and further, ethyl acetate, acetonitrile, acetone, dimethylformamide, or dimethyl sulfoxide.

Further, the series of reactions in steps (a), (b), and (c) may also be carried out in the presence of a base or acid, in addition to the above diluent. As the bases which can be used, there may be mentioned carbonates of alkali metals, such as sodium or potassium carbonate; hydroxides of alkali metals, such as sodium or potassium hydroxide; alcoholates of alkali metals, such as sodium methylate, sodium ethylate or potassium t-butylate; hydride of alkali metals, such as sodium or potassium hydride; alkylates of alkali metals, such as n-butyl lithium; and further, triethylamine, or pyridine. Further, as the acids, there may be mentioned inorganic acids, such as hydrochloric, hydrobromic, hydriodic, or sulfuric acid; organic acids, such as formic, acetic, butyric, or p-toluenesulfonic acid.

The reducing reaction in the step (a) may be carried out in the presence of, for example, a platinum catalyst, palladium carbon and potassium carbonate or palladium carbon, and a conventional oxidizing agent, such as Jone's reagent. That is, the compound of the formula (V) is dissolved in an organic solvent (for example, alcohol), a palladium carbon catalyst is added, and the reducing reaction is carried out for about 5 to 24 hours in a hydrogen stream. Then, the solvent is removed, an organic solvent is further added, Jone's reagent or the like is added, and the oxidation reaction is carried out. After the reaction is ceased by adding alcohol (for example, isopropyl alcohol), the resulting product is poured into ice water, extracted with a solvent (for example, ethyl acetate, diethyl ether). The product is dried over sodium sulfate or the like to remove the solvent, and the residue is purified by column chromatography to obtain the desired cyclohexanone compound (IV). In the cyclohexane ring of the cyclohexanone compound (IV), the configurations at the chiral ring carbon atom to which the phenyl group is bonded are not limited. Each of the optical isomers having any configuration or a mixture thereof may be used. The optical isomers may be resolved and purified by chromatography (for example, thin layer chromatography, column high performance liquid chromatography, or optical isomer separation column chromatography) and a general method of optical isomer separation. The compound of the general formula (V) may be prepared by the method described in, for example, *Monalsh Chem.* 9, 1043, 1960.

The cyclohexanone compound (IV) includes the optical isomers of the following general formulae (IVA) and (IVB):

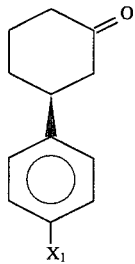
(IVA)

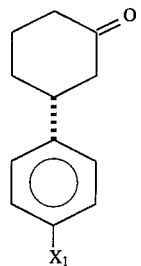
(IVB)

wherein $X_1$ has the same meaning as above.

The purification is performed by recrystallization, silica gel column chromatography, or the like. In the step (b), the configurations at the asymmetric carbon atom in the starting compound and the final compound are not limited. Each of the pure optical isomers having any configuration or mixtures thereof may be used. The optical isomers may be resolved and purified in the same manner as above. The oxolane compound (III) includes optical isomers of the following general formulae [III(t-(+))], [III(t-(−))], [III(c-(−))], and [III(c-(+))]:

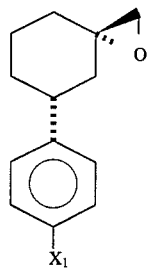
[III(t-(+))]

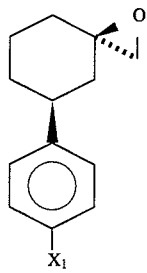
[III(t-(−))]

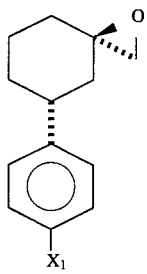
[III(c-(−))]

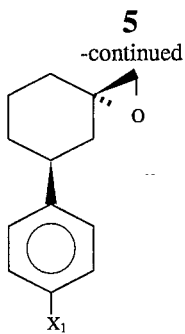

[III(c-(+))]

wherein $X_1$ has the same meaning as above.

The reaction of the step (c) may be performed by dissolving the imidazole of the formula (II) in the above-mentioned diluent, and adding the oxolane compound (III), in the presence of the above-mentioned base as occasion demands, or alternatively, by dissolving the oxolane compound (III) in the diluent, and then adding the imidazole of the formula (II). The reaction temperature is about 0° to 150° C., preferably about 40° to 120° C., and the reaction time is about 0.5 to 24 hours, preferably about 1 to 10 hours. After the above-mentioned reaction is completed, the reaction mixture is cooled and extracted with ice water with an organic solvent, such as ethyl acetate, chloroform, methylene chloride, diethyl ether, or benzene to separate the organic layer. Then, the organic layer is washed with water and dried. Further, the solvent is removed under reduced pressure and the resulting residue is purified to obtain the desired present imidazole compound (I). The purification is performed by recrystallization, silica gel column chromatography, or the like. In the step (c), the configurations at the chiral carbon atoms of the starting compound and the final compound are not limited. Each of the pure optical isomers having any configuration or mixtures thereof may be used. The present imidazole compound (I) includes the optical isomers of the following general formulae [I(t-(+))], [I(t-(−))], [I(c-(−))], and [I(c-(+))]:

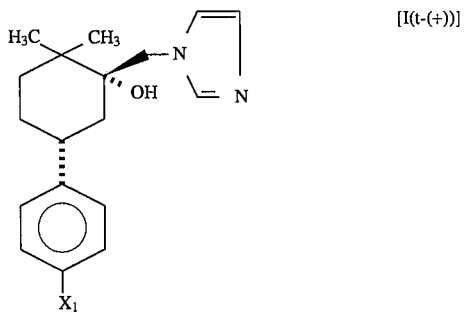

[I(t-(+))]

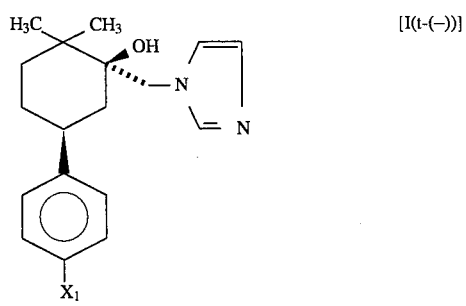

[I(t-(−))]

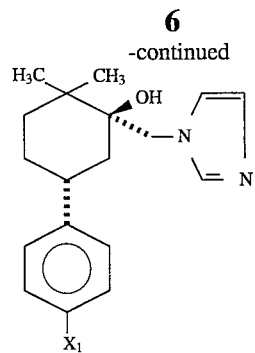

[I(c-(−))]

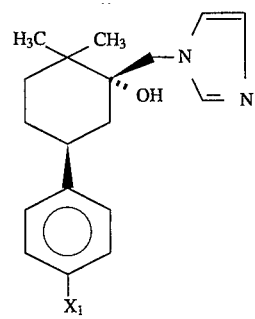

[I(c-(+))]

wherein $X_1$ has the same meaning as above.

The present imidazole compound (I) exhibits a pharmacological activity, in particular, an aromatase inhibitory activity, and an antitumor activity along with the aromatase inhibitory activity. Therefore, the present invention also relates to an aromatase inhibitory agent, particularly an antitumor agent, containing the present imidazole compound (I) or a pharmaceutically or veterinarily acceptable salt thereof, and a pharmaceutically or veterinarily acceptable diluent or carrier. Aromatase is an enzyme which aromatizes the ring A of many steroid hormones in the course of metabolism. Further, many cancers (for example, breast cancer, cancer of the uterus, prostate cancer, pancreatic cancer, ovarian cancer, or the like) depend on the steroid hormone having the aromatic ring A. Therefore, the present imidazole compound (I) exhibits an antitumor activity on these cancers.

The aromatase inhibitory activity was determined by the method of Covey, D. F. et al., [BBRC (1), 81–86, 1988]. That is, the aromatase inhibitory activity was determined as the 50% inhibitory concentration IC50 value of the enzyme activity of the compound to be tested, whereupon the $IC_{50}$ value of the present imidazole compound (I) was not more than $10^{-6}$M.

The present imidazole compound (I) may be mixed with a carrier generally acceptable for pharmaceutical compositions, and used in the form of various formulations. These compositions may be formulated into units of dosage containing about 1 to 600 mg, more preferably about 5 to 500 mg, of the present imidazole compound (I) in the form of dosage. The present imidazole compound (I) may be a salt, such as a sulfate, nitrate, or citrate. The pharmaceutical composition of the present invention may be administered orally, endermically, or intravenously.

When treating adults, it is suitable to administer about 0.1 to 100 mg/kg in one dosage or divide into several dosages. However, the actual dosage is determined by the physician with reference to the age of the individual patient, the seriousness of the symptoms, and the route of administration, so the range of the dosage mentioned above may be sometimes exceeded, but these cases are also included in the scope of the present invention. The acute toxicity ($LD_{50}$) of the present imidazole compound (I) was found using ICR mice to be over 500 mg/kg, so it is apparent that the present imidazole compound (I) is safe.

The novel imidazole derivative according to the present invention is low in toxicity, and has an aromatase inhibitory activity (therefore, an antitumor activity). Further, such activities are remarkable when continuously administered.

EXAMPLES

The present invention now will be further illustrated by, but is by no means limited to, the following examples. In the following examples, the NMR was measured using a JNMGSX 500 (Nihon Denshi), the infrared absorption spectra were measured using a Nihon Bunko A-202 apparatus, and the optical rotation was measured using a Nihon Bunko automatic polarimeter DIP-360.

Example 1

[1] Preparation of 6,6-dimethyl-3-(4-fluorophenyl)- 2-cyclohexene-1-one [V-1]

1-Bromo-4-fluorobenzene (7.06 g, 40 mmole) was dissolved in tetrahydrofuran (20 ml), and the resulting solution was stirred at −78° C. under argon. To this solution was added slowly n-butyllithium 125.2 ml, 1.6 mole solution, and the resulting mixture was allowed to stand for 15 minutes. A solution of 4,4-dimethyl-2-cyclohexene-1-one (5 g, 40 mmole) in tetrahydrofuran (20 ml) was slowly added to the above mixture, and then, the resulting solution was allowed to stand for 30 minutes. Thereafter, a saturated aqueous solution of ammonium chloride was added, the whole mixture was poured into ice water, and extracted with ethyl acetate. The organic layer was dried over sodium sulfate and the solvent was evaporated. Acetone (20 ml) was added to the residue. Then, the Jone's reagent previously prepared was added until its color was no longer changed (until it no longer became green). After 30 minutes, the reaction was quenched by adding isopropyl alcohol. The whole mixture was poured into ice water, and extracted with ethyl acetate. The organic layer was dried over sodium sulfate and the solvent was evaporated. The residue was purified by column chromatography (200 g of $SiO_2$, 10% ethyl acetate/hexane) to obtain the above-titled compound [V-1] (7.8 g; yield=89.4%). $^1$H-NMR (δppm; $CDCl_3$) 1.17 (s, 6 H), 1.97 (t, J=11.9 Hz, 2 H), 2.75 (t, J=11.9 Hz, 2 H), 6.30 (s, 1 H), 7.10, 7.55 (each m, 2 H) IR (νmax; KBr; $cm^{-1}$): 1650, 1600

[2] Preparation of 2,2-dimethyl-5-(4-fluorophenyl)cyclohexane- 1-one [IV-1]

The compound [V-1] (4 g, 18.3 mmole) obtained in Example 1[1] was dissolved in ethyl alcohol (20 ml). After 10% palladium carbon (100 mg) was added, the mixture was stirred overnight under hydrogen atmosphere. The reaction mixture was filtered in the next morning, and the solvent was removed under reduced pressure. Then, acetone (10 ml) was added to the residue, and Jone's reagent previously prepared was added until the reagent no longer changed in color (until no longer becoming green). After 30 minutes, the reaction was ceased by adding isopropyl alcohol. The mixture was poured into ice water and extracted with ethyl acetate. The organic layer was dried over sodium sulfate, and the solvent was evaporated. The residue was purified by column chromatography (100 g of $SiO_2$; 10% ethyl acetate/hexane) to obtain the above-titled compound [IV-1] (3.27 g, yield =80.9 %). $^1$H-NMR (δppm; $CDCl_3$) 1.12, 1.24 (each s, 3 H), 1.65–2.05 (m, 4 H), 2.47, 2.71 (each m, 1 H), 2.96 (m, 1 H), 7.02, 7.18 (each m, 2 H) IR (νmax; KBr; $cm^{-1}$): 1690, 1602

[3] Preparation of 2,2-dimethyl-5-(4-fluorophenyl)cyclohexane- 1,1"-oxolane [III(t-(±))-1]

Trimethylsulfoxonium iodide (1.2 g, 5.46 mmole) was dissolved in dimethyl sulfoxide (12 ml), and the solution was stirred in a water bath under argon. To the solution, sodium hydride (131 mg, 5.46 mmole) was slowly added. The resulting solution was allowed to stand for 20 minutes, and then, the solution was again cooled with a water bath. To the mixture, a solution of the compound [IV-1] (1 g, 4.55 mmole) obtained in Example 1[2] in dimethyl sulfoxide (2 ml) was slowly added, and the resulting mixture was stirred overnight at room temperature. The reaction mixture was poured into ice water in the next morning, and extracted with ethyl acetate. The organic layer was dried over sodium sulfate, and the solvent was evaporated. The residue was purified by column chromatography (100 g of $SiO_2$; 5% ethyl acetate/hexane) to obtain the above-titled compound [III(t-(±))-1] (764 mg, yield=71.8%). $^1$H-NMR (δppm; $CDCl_3$) 0.79, 1.16 (each s, 3 H), 1.48–1.82 (m, 4 H), 1.23, 2.28 (each m, 1 H), 2.42, 2.82 (each d, 1 H), 2.90 (m, 1 H), 6.97, 7.17 (each m, 2 H) IR (νmax; KBr; $cm^{-1}$): 1601

[4] Preparation of 2,2-dimethyl-5-(4-fluorophenyl)-1-( 1 H-imidazol-1-ylmethyl)-cyclohexane-1-ol [I(t-(±))-1]

The compound [III(t-(±))-1] (445 mg, 1.90 mmole) obtained in Example 1[3] was dissolved in dimethyl formamide (5 ml). To the solution was added, sodium imidazolate (350 mg, 3.89 mmole) and the whole was stirred at 90° C. for 4 hours. Thereafter, the reaction mixture was poured into ice water and extracted with ethyl acetate. The organic layer was dried over sodium sulfate, and the solvent was evaporated. The residue was recrystallized from methyl alcohol/ ethyl acetate/hexane to obtain the above-titled compound [I(t-(±))-1] (529 mg, yield=92.2%). $^1$H-NMR (δppm; $CDCl_3$) 1.05, 1.18 (each s, 3 H), 1.20–2.02 (m, 6 H), 2.81 (m, 1 H), 4.05, 4.18 (each d, J=28.4 Hz, 1 H), 6.93, 7.10, 7.64 (each s, 1 H), 6.95, 7.19 (each m, 2 H) IR (νmax; KBr; $cm^{-1}$): 3400, 1600

Example 2

[1] Preparation of 4,4-dimethyl-1-(4-chlorophenyl)- 2-cyclohexene-1-ol

To a 100 ml eggplant type flask, 4-bromochlorobenzene (7.66 g, 40 mole) and dry tetrahydrofuran (25 ml) were added, the mixture was stirred at room temperature under argon. The mixture was cooled to −78° C. in a dry ice/ acetone bath, and then, a solution (25 ml) of n-butyllithium (40 mmole) in n-hexane is slowly added thereto. After the mixture was stirred for 30 minutes, a solution of 4,4-dimethyl-2-cyclohexene-1-one (4.96 g, 40 mmole) in dry tetrahydrofuran was added dropwise. After 90 minutes, the completion of the reaction was confirmed by thin layer chromatography. Then, a saturated aqueous solution of ammonium chloride (10 ml) was added to stop the reaction. The resulting mixture was poured into ice water (10 ml), and extracted with diethyl ether (100 ml×2 and 50 ml×1). The organic layer was washed with brine, and dried over sodium sulfate. The solvent was evaporated and the residue was purified by silica gel chromatography [100 g of Merck Kieselgel 60, n-hexane/ethyl acetate (4:1)] to obtain the above-titled compound (9.34 g, yield=98.6%). $^1$H-NMR (δppm; $CDCl_3$) 1.04 (s, 3 H), 1.08 (s, 3 H), 1.41 (m, 1 H), 1.65 (m, 1 H), 1.90 (m, 2 H), 5.57 (d, J=10.08 Hz, 1 H), 5.74 (d, J=10.08 Hz, 1 H), 7.29 (d, J=8.71 Hz, 2 H), 7.40 (d, J=8.71 Hz, 2 H) IR (νmax; KBr; $cm^{-1}$): 3450, 3000, 1922, 1660, 1500, 1480, 1460, 1370, 1180, 1100

[21] Preparation of 2,2-dimethyl-5-(4-chlorophenyl)- 5-cyclohexene-1-one [V-2]

4,4-Dimethyl-1-(4-chlorophenyl)-2-cyclohexene-1-ol (19.48 g, 82.29 mmole) obtained in Example 2[1] was placed in a 200 ml eggplant type flask. After acetone (85 ml) was added, the mixture was stirred. Then, Jone's reagent (25 ml) was added dropwise to this solution in an ice bath. After 15 minutes, the completion of the reaction was confirmed by thin layer chromatography. Isopropyl alcohol was added to decompose the excess reagent, and the mixture was poured into cooled water (85 ml) and extracted with diethyl ether (100 ml×2). The organic layer was washed with brine, and dried over sodium sulfate. The solvent was evaporated and the residue was purified by silica gel chromatography [170 g of Merck Kieselgel 60, n-hexane/ethyl acetate (8:1)] to obtain the above-titled compound [V-2] (16.61 g, yield= 86.0%) as a white crystal. $^1$H-NMR (δppm; CDCl$_3$) 1.17 (s, 3 H×2), 1.97 (m, 2 H), 2.75 (m, 2 H), 6.32 (s, 1 H), 7.38 (d, J=8.70 Hz, 2 H), 7.48 (d, J=8.70 Hz, 2 H) IR (vmax; KBr; cm$^{-1}$): 2990, 1655, 1615, 1595, 1510, 1210, 1150, 1095 Mass spectrum (M$^+$): 234, 206, 178, 150, 115

[3] Preparation of 2,2-dimethyl-5-(4-chlorophenyl)cyclohexane-1-ol

To the compound [V-2] (5.06 g, 21.5 mmole) obtained in Example 2[2], 10% palladium carbon was added and then, ethyl alcohol was gradually added while cooling in an ice bath. The mixture was stirred overnight under a hydrogen atmosphere at room temperature. After the completion of the reaction was confirmed by thin layer chromatography, the mixture was filtered through a fluted filter. The filtrate was concentrated and the residue was purified by silica gel chromatography [50 g of Merck Kieselgel 60, n-hexane/ethyl acetate (5:1)] to obtain the above-titled compound (4.72 g, yield=91.7%) as yellow oil. $^1$H-NMR (δppm; CDCl$_3$) 0.95 (s, 3 H), 1.05 (s, 3 H), 1.35 (m, 1 H), 1.55 (m, 3 H), 1.88 (m, 1 H), 2.58 (m, 1 H), 3.45 (dd, J=4.13, 7.33 Hz, 1 H), 7.14 (d, J=8.71 Hz, 2 H), 7.26 (d, J=8.71 Hz, 2 H) IR (vmax; KBr; cm$^{-1}$): 2940, 1500, 1460, 1390, 1370, 1090

[4] Preparation of 2,2-dimethyl-5-(4-chlorophenyl)cyclohexane-1-one [IV-2]

In a 100 ml eggplant flask, 2,2-dimethyl-5-(4-chlorophenyl)-cyclohexane-1-ol (3.94 g, 16.5 mmole) obtained in Example 2[3] was placed and then acetone (17 ml) was added. After stirring, Jone's reagent (3 ml) wad added dropwise while cooling in an ice bath. After 90 minutes, the completion of the reaction was confirmed by thin layer chromatography. Isopropyl alcohol was added to decompose the excess reagent, and the mixture was poured into cooled water (20 ml) and extracted with diethyl ether (50 ml×2). The organic layer was washed with brine, and dried over sodium sulfate. The solvent was evaporated and the residue was purified by silica gel chromatography [100 g of Merck Kieselgel 60, n-hexane/ethyl acetate (10:1)] to obtain the above-titled compound [IV-2] (2.40 g, yield=61.4%) as a white crystal. $^1$H-NMR (δppm; CDCl$_3$) 1.21 (s, 3 H), 1.24 (s, 3 H), 1.69 (m, 1 H), 1.85 (m, 1 H), 1.91 (m, 1 H), 1.99 (m, 1 H), 2.47 (m, 1 H), 2.71 (dd, J=1.37, 12.83 Hz, 1 H), 2.95 (m, 1 H), 7.15 (d, J=8.25 Hz, 2 H), 7.29 (d, J=8.25 Hz, 2 H) IR (vmax; KBr; cm$^{-1}$): 3000, 1710, 1510, 1150, 1090 Mass spectrum (M$^+$): 236, 192, 180, 165, 152, 138

[5] Preparation of 2,2-dimethyl-5-(4-chlorophenyl)cyclohexane- 1,1'-oxolane [III(t-(±))-2]

To sodium hydride (166.8 mg, 6.95 mmole) washed with n-hexane, dimethyl sulfoxide (2 ml) and dry tetrahydrofuran (3 ml) were added, and the mixture was stirred for 15 minutes at room temperature. A solution of trimethyl sulfonium iodide (1.42 g, 6.95 mmole) in dimethylsulfoxide (4 ml) was added while cooling in an ice bath. Further, a solution of the compound [IV-2] (1.097 g, 4.63 mmole) obtained in Example 2[4] in dimethyl sulfoxide (2 ml) was added dropwise, and the apparatus was washed with dimethyl sulfoxide (2 ml). The mixture was stirred overnight at room temperature. After the completion of the reaction was confirmed by thin layer chromatography, cold water (10 ml) was added to stop the reaction. The mixture was extracted with diethyl ether (50 ml×3). The organic layer was washed with brine, and dried over sodium sulfate. The solvent was evaporated and the residue was purified by silica gel chromatography [50 g of Merck Kieselgel 60, n-hexane/ethyl acetate (50:1)] to obtain the above-titled compound [III(t-(±))-2] (296.9 mg, yield=25.6%) as transparent oil. $^1$H-NMR (δppm; CDCl$_3$) 0.80 (s, 3 H), 1.14 (s, 3 H), 1.23 (m, 1 H), 1.54 (m, 1 H), 1.72 (m, 3 H), 2.28 (m, 1 H), 2.48 (d, J=4.58 Hz, 1 H), 2.72 (m, 1 H), 2.92 (d, J=4.58 Hz, 1 H), 7.15 (d, J=8.02 Hz, 2 H), 7.27 (d, J=8.02 Hz, 2 H) IR (vmax; KBr; cm$^{-1}$): 2950, 1505, 1480, 1460, 1155, 1095

[6] Preparation of 2,2-dimethyl-5-(4-chlorophenyl)- 1-(1 H-imidazol-1-ylmethyl)-cyclohexane-1-ol [I(t-(±))-2]

To the compound [III(t-(±))-2] (1.02 g, 4.67 mmole) obtained in Example 2[5], sodium imidazolate (550 mg, 6.1 mmole) and then dimethyl sulfoxide (5 ml) were added. The mixture was stirred overnight under argon in an oil bath at 80° C. After the completion of the reaction was confirmed by thin layer chromatography, distilled water (20 ml) was added to cease the reaction. The mixture was extracted with ethyl acetate (50 ml×3). The organic layer was washed with brine, and dried over sodium sulfate. The solvent was evaporated and the residue was purified by silica gel chromatography [10 g of Merck Kieselgel 60, 5% methyl alcohol/ethyl acetate] to obtain the above-titled compound [I(t-(−))-2] (610 mg, yield=50%) as a white crystal. m.p. 224°–225° C. IR (vmax; KBr; cm$^{-1}$): 3140, 3000, 2950, 2880, 1680, 1525, 1505, 1440 Mass spectrum (M$^+$): 318, 300, 285, 219, 125, 82 (100) $^1$H-NMR (δppm; CDCl$_3$) 1.10 (s, 3 H), 1.15 (s, 3 H), 1.25–1.39 (m, 2 H), 1.60– 1.78 (m, 2 H), 1.99 (dt, 1 H), 2.7–2.8 (m, 1 H), 3.83 (d, J=14.2 Hz, 1 H), 4.15 (d, J=14.2 Hz, 1 H), 6.84 (s, 1 H), 6.88 (s, 1 H), 7.07 (d, 2 H), 7.24 (m, 2 H), 7.42 (s, 1 H)

Example 3

[1] Preparation of 6,6-dimethyl-3-(4-hydroxyphenyl)- 2-cyclohexene-1-one [V-3]

4-Bromophenol benzyl ether (3.34 g) was dissolved in tetrahydrofuran (20 ml), and the resulting solution was stirred at −78° C. in an argon gas stream. n-Butyllithium (8.33 ml, 1.6 mole solution) was added slowly and the mixture was allowed to stand for 15 minutes. A solution of 4,4-dimethyl-2-cyclohexene-1-one (1.57 g) in tetrahydrofuran (5 ml) was slowly added to the above solution, and then, the resulting mixture was allowed to stand for 30 minutes. Thereafter, a saturated aqueous solution of ammonium chloride was added, the mixture was poured into ice water, and extracted with ethyl acetate. The organic layer was dried over sodium sulfate and the solvent was evaporated. Acetone (10 ml) was added to the residue. Then, the Jone's reagent previously prepared was added until its color was no longer changed (until it no longer became green). After 30 minutes, the reaction was ceased by adding isopropyl alcohol. The whole was poured into ice water, and the crude product was extracted with ethyl acetate. The organic layer was dried over sodium sulfate and the solvent was evaporated. The residue was purified by column chromatography (50 g of SiO$_2$, 5% ethyl acetate/hexane) to obtain the above-titled compound [V-3] (700 mg). $^1$H-NMR (δppm; CDCl$_3$) 1.12 (s, 3 H), 1.24 (s, 3 H), 1.68 (m, 2 H), 1.81–1.99 (m, 2 H), 5.28 (b, 2 H), 6.79 (d, J=8.71 Hz, 2 H), 6.84 (d, J=8.71 Hz, 1 H), 7.07 (d, J=8.71 Hz, 2 H), 7.41 (d, J=8.16 Hz, 1 H)

[2] Preparation of 2,2-dimethyl-5-(4-hydroxyphenyl)cyclohexane-1-one [IV-3]

The compound [V-3] (700 mg) obtained in Example 3[1] was dissolved in ethyl alcohol (5 ml). After 10% palladium carbon (20 mg) was added, the mixture was stirred overnight in a hydrogen gas stream. The reaction mixture was filtered in the next morning, and the solvent was evaporated. Then, acetone (3 ml) was added to the residue, and Jone's reagent previously prepared was added until the reagent no longer changed in color (until no longer becoming green). After 30 minutes, the reaction was stopped by adding isopropyl alcohol. The mixture was poured into ice water and extracted with ethyl acetate. The organic layer was dried over sodium sulfate, and the solvent was evaporated. The residue was purified by column chromatography (50 g of $SiO_2$; 20% ethyl acetate/hexane) to obtain the above-titled compound [IV-3] (210 mg). $^1$H-NMR ($\delta$ppm; $CDCl_3$) 1.12 (s, 3 H), 1.24 (s, 3 H), 1.60–1.70 (m, 2 H), 1.80–2.00 (m, 4 H), 2.71 (t, J=12.83 Hz, 1 H), 4.80 (b, 1 H), 6.79 (d, J=8.70 Hz, 2 H), 7.09 (d, J=8.70 Hz, 2 H) IR ($\nu$max; KBr; $cm^{-1}$): 3275, 1790, 1690, 1610, 1595, 1520, 1445

[3] Preparation of 2,2-dimethyl-5-(4-hydroxyphenyl)-1-(1 H-imidazoly-1-yl-methyl)-cyclohexane-1-ol [I-3]

Trimethylsulfoxonium iodide (636 mg) was dissolved in dimethyl sulfoxide (5 ml), and the solution was stirred in a water bath under argon. To the solution, sodium hydride (69 mg) was slowly added. The resulting solution was allowed to stand for 20 minutes, and then, the solution was cooled with a water bath. To the mixture, a solution of the compound [IV-3] (210 mg) obtained in Example 3[2] in dimethyl sulfoxide (1 ml) was slowly added, and the resulting solution was stirred overnight at room temperature. The reaction mixture was poured into ice water in the next morning, and extracted with ethyl acetate. The organic layer was dried over sodium sulfate, and the solvent was evaporated. The residue was dissolved in dimethyl formamide (5 ml). To the solution, sodium imidazolate (250 mg) was added, and the whole was stirred at 90° C. for 8 hours. Thereafter, the reaction mixture was poured into ice water and extracted with ethyl acetate. The organic layer was dried over sodium sulfate, and the solvent was evaporated. The residue was purified by column chromatography (20 g of $SiO_2$; 3% methyl alcohol/ethyl acetate) to obtain the above-titled compound [I-3] (90 mg). $^1$H-NMR ($\delta$ppm; $CDCl_3$) 1.10 (s, 3 H), 1.17 (s, 3 H), 1.32 (dt, J=13.75, 3.21 Hz, 1 H), 1.39 (dd, J=14.2, 3.21 Hz, 1 H), 1.70–1.80 (m, 3 H), 2.00 (m, 1 H), 2.78 (m, 1 H), 3.86 (d, J=14.2 Hz, 1 H), 4.16 (d, J=14.20 Hz, 1 H), 6.87 (s, 1 H), 6.93 (s, 1 H), 7.19 (m, 4 H), 7.44 (s, 1 H) IR ($\nu$max; KBr; $cm^{-1}$): 3420, 3180, 2950, 1600, 1519, 1500, 1470, 1450, 1438, 1390, 1285, 1239, 1105

PHARMACOLOGICAL EXAMPLE

The following pharmacological tests were performed using the compounds of the present invention prepared in Examples 1 to 3. Hereinafter, the compounds of the present invention prepared in Examples 1 to 3 will be abbreviated as shown in the following Table 1:

TABLE 1

| Compounds of present invention | Abbreviation |
|---|---|
| I(t-(±))-1 | Compound 1 |
| I(t-(±))-2 | Compound 2 |
| I(c-(±))-3 | Compound 3 |

As a comparative compound, 3-(4-fluorophenyl)-1-(1 H-imidazol-1-ylmethyl)-cyclohexane-1-ol (hereinafter referred to as Compound C) was used.

Example 4

Aromatase Inhibitory Activity

The aromatase activity was measured based on the method of Covey et al. (Covey, D. F. et al., *BBRC*, 157, (1), 81 to 86, 1988). The aromatase inhibitory activity was determined from the 50% inhibitory concentration ($IC_{50}$ value) of the enzyme activity.

That is, human placental microsome was used as the aromatase enzyme source and [19-$^{14}$C]4-androstene-3,17-dione was used as the substrate. The radioactivity of the $H^{14}COOH$ released in the reaction solution as a result of aromatization was measured to find the enzyme activity radiometrically. Then, a graph of the concentrations of the tested compounds versus the inhibition of the enzyme activity was prepared and the $IC_{50}$ values were found on the graph.

More particularly, a reaction was carried out for 30 minutes in a reaction solution of 0.5 ml of 67 mM phosphate buffer (pH 7.2) while shaking at 37° C., in a system comprised of [19-$^{14}$C]4-androstene-3,17-dione ($1\times10^{-6}$M, 2 kBq/ml), human placenta microsome (0.1 mg/ml protein concentration), coenzyme NADPH ($2\times10^{-3}$M), glucose-6-phosphate ($4\times10^{-3}$M), and glucose-6-phosphate dehydrogenase (4 U/ml). The compounds to be tested were added as a solution in dimethyl sulfoxide (final concentration of dimethyl sulfoxide = 0.1 to 0.55%). The $H^{14}COOH$ released in the reaction solution was recovered in the aqueous phase by adding 5 ml of chloroform to the reaction solution at the time of the cessation of the reaction and stirring. 0.1 ml of the aqueous phase was taken and mixed with 4 ml of liquid scintillation cocktail [Atomlight (Dupont)] to measure the radioactivity. The results are shown in Table 2.

TABLE 2

| Tested compounds | $ID_{50}$ value (μmol/l) |
|---|---|
| Compound 1 | $3.0 \times 10^{-6}$ |
| Compound 2 | $2.5 \times 10^{-6}$ |
| Compound 3 | $2.0 \times 10^{-6}$ |
| Compound C | $1 \times 10^{-5}$ |

Example 5

Minimum Inhibitory Concentration

The minimum inhibitory concentrations (MIC) in vitro of the compounds 1 to 3 of the present invention against microorganisms belonging to the genera Candida and Aspergillus were determined. (1) The strains of the microorganisms used were as follows. The inoculation solutions were prepared at a concentration of $1\times10^6$ cells/ml.

1) *Candida albicans* IFO 1060
2) *Candida albicans* IFO 1270
3) *Candida albicans* ATCC 762
4) *Candida tropicaris* IFO 1400
5) *Candida krusei* IFO 1395
6) *Candida parapsilosis* IFO 1396
7) *Aspergillus fumigatus* IFO 5840
8) *Aspergillus fumigatus* IFO 9733 (2) As the medium, a Sabouraud dextrose agar medium (Difco: dextrose 2%, agar 1.8%, not adjusted in pH) was used. The samples of the compounds to be tested were used after dissolved in dimethyl sulfoxide. The concentrations of the samples were from 6.25 to 400/ml. (3) Procedure The agar media containing the different concentrations of the compounds to be tested were inoculated with the microorganisms, using a microplanter (Sakuma Seisakusho). The microorganisms belonging to the genera Candida were cultured at 27° C. for 3 days, and the microorganisms belonging to the genus Aspergillus at 27° C. for 5 days. The minimum concentration on the agar medium exhibiting inhibition of growth was used as the minimum inhibitory concentration (MIC). The results are shown in Table 3.

TABLE 3

MIC of Present Compounds Against Various Fungi (μg/ml)

| Fungi | Compound 1 | Compound 2 | Compound 3 | Compound C |
|---|---|---|---|---|
| 1) | 50 | 50 | 50 | 200 |
| 2) | 50 | 25 | 100 | 200 |
| 3) | 50 | 25 | 50 | 200 |
| 4) | 50 | 100 | 50 | 400< |
| 5) | 50 | 100< | 200 | 400< |
| 6) | 50 | 100< | 200 | 400< |
| 7) | 50 | 100 | 200 | 400< |
| 8) | 50 | 100 | 200 | 400< |

Example 6

Preparation of Capsules

The compound 1 (100 mg) of the present invention, 50 mg of polyoxyethylene sorbitamine monooleate, and 250 mg of starch were thoroughly mixed and filled in capsules to prepare capsules.

Although the present invention has been described with reference to specific embodiments, various changes and modifications obvious to those skilled in the art are deemed to be within the spirit, scope, and concept of the invention.

What is claimed is:

1. A method of inhibiting aromatase, comprising administering to a mammal in need thereof a pharmaceutical composition comprising an effective aromatase inhibiting amount of a compound of the formula (I):

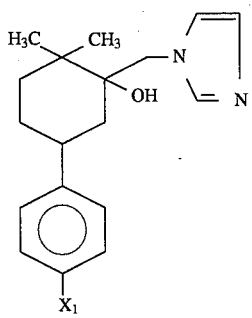

wherein $X_1$ is a chlorine or fluorine atom, or a hydroxy group, or a pharmaceutically acceptable salt thereof, and a pharmaceutically acceptable carrier.

2. A method according to claim 1, wherein a racemic mixture of compounds of the formulas [I(t-(+))] and [I(t-(−))] are administered:

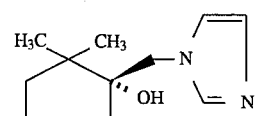

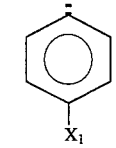

wherein $X_1$ is a chlorine or fluorine atom, or a hydroxy group, or a pharmaceutically acceptable salt thereof, and a pharmaceutically acceptable carrier.

3. A method according to claim 1, wherein a compound of the formula [I(t-(+))] is administered:

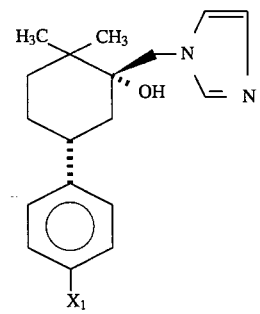

wherein $X_1$ is a chlorine or fluorine atom, or a hydroxy group, or a pharmaceutically acceptable salt thereof, and a pharmaceutically acceptable carrier.

4. A method according to claim 1, wherein a compound of the formula [I(t-(−))] is administered:

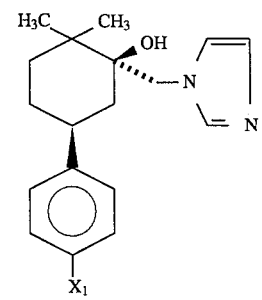

wherein $X_1$ is a chlorine or fluorine atom, or a hydroxy group, or a pharmaceutically acceptable salt thereof, and a pharmaceutically acceptable carrier.

5. A method according to claim 1, wherein a racemic mixture of compounds of the formulas [I(c-(+))] and [I(c-(−))] are administered:

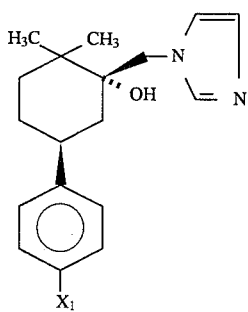 [I(c-(+))]

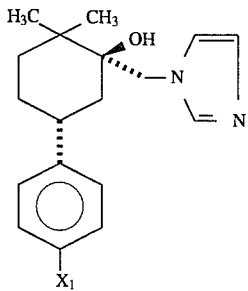 [I(c-(-))]

wherein $X_1$ is a chlorine or fluorine atom, or a hydroxy group, or a pharmaceutically acceptable salt thereof, and a pharmaceutically acceptable carrier.

6. A method according to claim 1, wherein a compound of the formula [I(c-(+))] is administered:

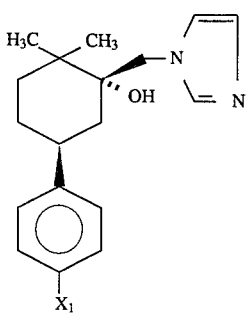 [I(c-(+))]

wherein $X_1$ is a chlorine or fluorine atom, or a hydroxy group, or a pharmaceutically acceptable salt thereof, and a pharmaceutically acceptable carrier.

7. A method according to claim 1, wherein a compound of the formula [I(c-(-))] is administered:

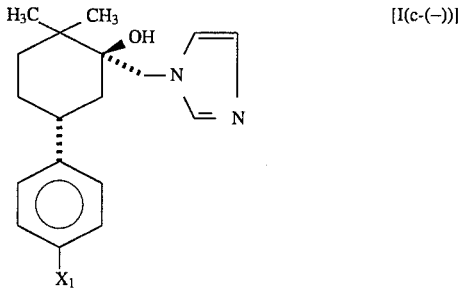 [I(c-(-))]

wherein $X_1$ is a chlorine or fluorine atom, or a hydroxy group, or a pharmaceutically acceptable salt thereof, and a pharmaceutically acceptable carrier.

8. A method according to claim 1, wherein a tumor in the mammal is treated.

9. A method according to claim 2, wherein a tumor in the mammal is treated.

10. A method according to claim 3, wherein a tumor in the mammal is treated.

11. A method according to claim 4, wherein a tumor in the mammal is treated.

12. A method according to claim 5, wherein a tumor in the mammal is treated.

13. A method according to claim 6, wherein a tumor in the mammal is treated.

14. A method according to claim 7, wherein a tumor in the mammal is treated.

* * * * *

UNITED STATES PATENT AND TRADEMARK OFFICE
CERTIFICATE OF CORRECTION

PATENT NO. : 5,547,973
DATED : August 20, 1996
INVENTOR(S) : Koichi Niimura, Takao Ando, Toyohiko Nitta, Yuko Ikeda It is certified that error appears in the above-identified patent and that said Letters Patent is hereby corrected as shown below:

Column 1, line 30, delete "3-187464" and insert therefor --3-197464--.

Column 13, line 2, delete "400/ml" and insert therefor --400 µg/ml--.

Signed and Sealed this

Eleventh Day of November, 1997

Attest:

BRUCE LEHMAN

Attesting Officer    Commissioner of Patents and Trademarks